US00PP16214P3

(12) United States Plant Patent
Coiner

(10) Patent No.: US PP16,214 P3
(45) Date of Patent: Jan. 24, 2006

(54) HYBRID TEA ROSE PLANT NAMED 'WHY NOT CHERISE?'

(50) Latin Name: *Rosa hybrida*
Varietal Denomination: Why Not Cherise?

(75) Inventor: James W. Coiner, La Verne, CA (US)

(73) Assignee: Coiner Nursery, LaVerne, CA (US)

( * ) Notice: Subject to any disclaimer, the term of this patent is extended or adjusted under 35 U.S.C. 154(b) by 124 days.

(21) Appl. No.: 10/016,074

(22) Filed: Dec. 5, 2001

(65) Prior Publication Data

US 2003/0106119 P1 Jun. 5, 2003

(51) Int. Cl.
*A01H 5/00* (2006.01)

(52) U.S. Cl. ..... Plt./139

(58) Field of Classification Search ..... Plt./130, Plt./136, 135, 139, 140
See application file for complete search history.

*Primary Examiner*—Howard J. Locker
(74) *Attorney, Agent, or Firm*—Christie, Parker & Hale, LLP

(57) ABSTRACT

A new and distinct Hybrid Tea Rose plant variety with dark red flowers.

1 Drawing Sheet

Classification: The present invention relates to a *Rosa hybrida* plant.

Variety denomination: The new plant has the varietal denomination 'Why Not Cherise?'.

BACKGROUND OF THE INVENTION

The present invention relates to a new and distinct variety of rose plant of the hybrid tea rose of the genus *Rosaceae* which was created by crossing as seed and pollen parents two (2) unknown rose varieties. The varietal denomination of the new variety is 'Why Not Cherise?'.

SUMMARY OF THE INVENTION

Among the novel characteristics possessed by this new variety which distinguishes it from other varieties of which I am aware, is its dark red flowers.

Asexual reproduction by propagation by budding of the new variety onto 'Dr. Huey' rootstock as performed in Wasco, Calif. shows that the foregoing and other distinguishing characteristics come true to form and are established and transmitted through succeeding propagations.

BRIEF DESCRIPTION OF ILLUSTRATION

The accompanying illustration shows typical specimens of the flowers and foliage of the new variety depicted in color as nearly true as it is reasonably possible to make the same in a color illustration of this character.

DESCRIPTION OF THE NEW VARIETY

The following is a detailed description of 2-year budded plants of the new variety, with color terminology in accordance with The Royal Horticultural Society Colour Chart (R.H.S.C.C.). The terminology used in color description herein refers to plate numbers in the aforementioned color chart. Phenotypic expression may vary with light availability, environmental and cultural conditions.

The following observations are made of specimens grown outdoors in Wasco, Calif., during the month of November budded on 'Dr. Huey' understock.

Plant:

*Form.*—Upright.
*Growth.*—Very vigorous.
*Size.*—Height about 5 feet; width about 3 feet.
*Disease resistance.*—Cultivar exhibits average resistance/susceptibility to disease.
*Foliage.*—Size: Terminal leaflet length about 3 inches; width about 1½ inches.
*Quantity.*—Usually 5 leaflet leaves.
*Color.*—New foliage: Upper side near 146B; under side near 182C.
Mature foliage: Upper side near 147A; under side near 147C.
*Shape.*—Elliptic.
*Texture.*—Upper side smooth, semi-glossy; under side matte.
*Edge.*—Serrated.
*Serration.*—Serrate.
*Petioles.*—Top surface color near 146B; Under side near 147C.
*Stipules.*—Medium.
*Auricle.*—Small, slightly serrated.
*Rachis.*—Smooth.

Wood:

*New shoots.*—Bark: Smooth. Wood: Near 137B with anthocyanin blush near 46A.
*Old wood.*—Bark: Smooth. Wood: Near 137C.
*Flowering stem.*—Length about 18 inches.
*Winter hardiness.*—Completely winter hardy.
*Preferred growing conditions.*—Full sun.
*Growth habit.*—Upright.
*Leaves per stem.*—About 7.
*Prickles/thorns.*—Plant bears both large and small prickles; large prickles about 3/16 in., small prickles about 1/16 in., randomly distributed, color near 20D.

Flower/inflorescence:

*Blooming habit.*—Continuous. Bud: About 1½ inches long, 1⅜ inches wide. Form: High centered. Color: Before sepals divide color near 46B; when sepals first divide color near 47B; when petals begin to unfurl color near 47D. Sepals: Usually 5 per bloom, length about 1⅞ inch, width about ½ inch tapering down to ⅛ inch, top and bottom color from near 143A (tip) to near 143C (base). Peduncle: Typically with numerous acicular projections. Length: About 4½ inches. Strength: Erect. Color: Near 139D.

*Flower.*—Size: About 5⅔ inches. Borne: Single. Form: Very high centered.

*Petalage.*—About 42. Petaloids in center: Few; between 3 to 4, color near 57A. Persistence: Petals do not drop.

*Fragrance.*—Medium.

*Lasting quality.*—About 3 weeks on plant; about 7 days after cutting.

*Color.*—During first 2 days: Inner petals at flower center topside near 46C; bottom near 46D; outer petals topside near 47D, bottom near 48C.

*Base of petals* (*point of attachment*).—Near 2A.

*General tonality from a distance.*—Near 53C.

*Color change.*—Fades slightly; after 3 or more days fades to near 49A.

*Petals.*—Margin Smooth. Texture: Thick. Shape: Oblong 1¼ inch wide. 1½ inch long. Arrangement: Imbricated. Appearance: Velvety front, satiny back.

Reproductive organs:

*Arrangement of stamens, filaments and anthers.*—Regularly arranged around styles, usually about 110 anthers and filaments.

*Color.*—Filaments near 48A; Anthers near 48C.

*Pollen.*—No pollen.

*Styles.*—Medium length; color near 47C.

*Hips/seed vessels/ovaries.*—Shape: Round. Size: Small; about ½ inch. Color: Near 140A. Seeds: No seeds.

I claim:

1. A new and distinct Hybrid Tea Rose plant of the variety substantially as shown and described.

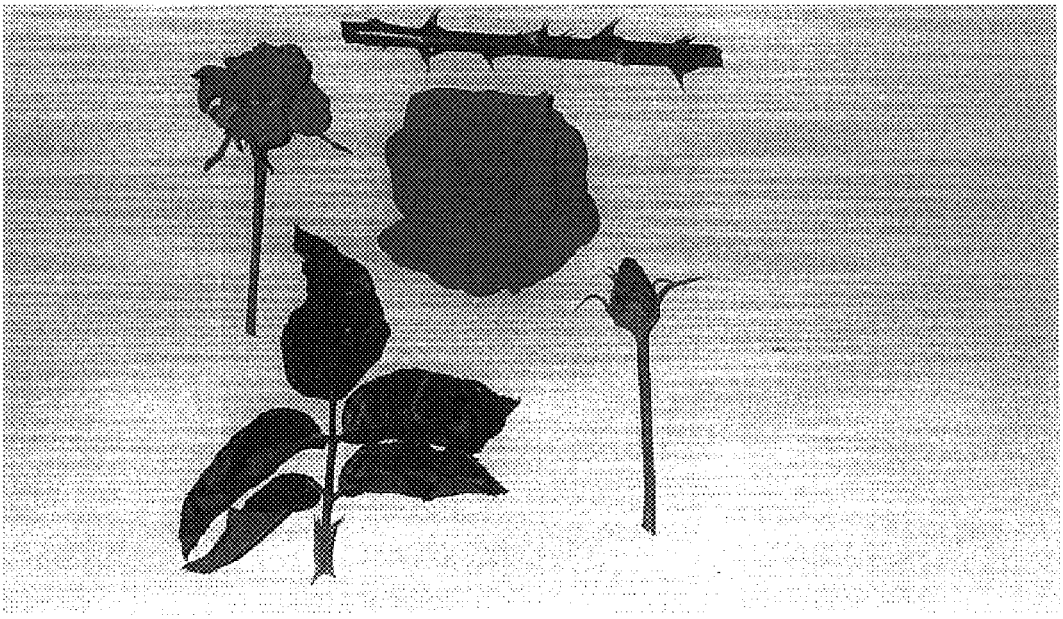

* * * * *